United States Patent
Raufman et al.

(10) Patent No.: US 6,624,156 B2
(45) Date of Patent: Sep. 23, 2003

(54) METHODS OF MAKING AND METHOD OF USING HYBRID CHOLINERGIC AGENTS AND COMPOSITIONS

(75) Inventors: Jean-Pierre Raufman, Little Rock, AR (US); Piotr Zimniak, Little Rock, AR (US); Kunrong Cheng, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 31 days.

(21) Appl. No.: 10/179,627

(22) Filed: Jun. 25, 2002

(65) Prior Publication Data

US 2002/0183295 A1 Dec. 5, 2002

Related U.S. Application Data

(62) Division of application No. 09/847,841, filed on May 1, 2001.

(51) Int. Cl.$^7$ .............................. A61K 31/56; C07J 9/00
(52) U.S. Cl. ...................... 514/176; 514/182; 552/549; 552/551; 552/552
(58) Field of Search ................................ 514/176, 182; 552/549, 551, 552

*Primary Examiner*—Barbara P. Badio
(74) *Attorney, Agent, or Firm*—Gilbreth & Associates, P.C.; J. M. (Mark) Gilbreth; Mary A. Gilbreth

(57) ABSTRACT

The present invention provides hybrid molecules and methods of synthesizing such hybrid molecules from a cholinergic agent and a bile acid. The hybrid molecules function as cholinergic agents and may be either cholinergic agonists or cholinergic antagonists. Further disclosed herein are compositions comprising hybrid cholinergic agents and methods of making such compositions. Methods of treating a patient having a cholinergic disorder are also disclosed.

11 Claims, 2 Drawing Sheets

METHODS OF MAKING AND METHOD OF USING HYBRID CHOLINERGIC AGENTS AND COMPOSITIONS

REFERENCE TO RELATED APPLICATIONS

The present application is a Divisional Application of and claims benefit under 35 U.S.C. 120 of U.S. patent application Ser. No. 09/847,841, filed, May 1, 2001, entitled "Hybrid Cholinergic Agents and Compositions."

BACKGROUND OF THE INVENTION

1. Field of the Invention

The present invention relates to acetylcholine, cholinergic signal transduction, and bile acids. In another aspect, the present invention relates to hybrid molecules, the synthesis of hybrid molecules from a progenitor cholinergic agent and a bile acid, and compositions and methods comprising said hybrid molecules. In even another aspect, the present invention relates to hybrid cholinergic molecules, compositions comprising hybrid cholinergic molecules, and methods of using said molecules and compositions as agonists or antagonists of muscarinic receptor-dependent signal transduction. In still another aspect, the present invention relates to hybrid cholinergic molecules, compositions comprising said molecules, and methods of treating a medical disorder comprising administration of these molecules and/or compositions.

2. Description of the Related Art

Acetylcholine (ACh) serves as the neurotransmitter at all autonomic ganglia, at the postganglionic parasympathetic nerve endings, and at the postganglionic sympathetic nerve endings innervating the eccrine sweat glands. Two different types of cholinergic receptors for ACh, the nicotinic and muscarinic receptors, exist on the postganglionic neurons within the autonomic ganglia and at the postjunctional autonomic effector sites. The nicotinic receptors are stimulated predominantly by nicotine and are found in the synapses between the preganglionic and postganglionic neurons of both the sympathetic and parasympathetic nervous systems, and are also present in many membranes of skeletal muscle fibers at the neuromuscular junction. The muscarinic receptors are stimulated primarily by the alkaloid muscarine and are found in all effector cells stimulated by the postganglionic neurons of the parasympathetic nervous system, and effector cells stimulated by the postganglionic cholinergic neurons of the sympathetic nervous system. Clearly, cholinergic receptors play an important role in the functioning of muscles, organs and the central nervous system. Cross-talk also exists between cholinergic receptors and the receptors of other neurotransmitters such as dopamine, serotonin and catecholamines.

Muscarinic cholinergic receptors can be characterized pharmacologically by their interaction with a variety of agonists and antagonists. Molecular cloning studies have revealed the existence of five muscarinic receptor gene, designated M1–M5, base on the order of the cloning of the genes.

Disruption of the cholinergic neurotransmitter signalling system has been implicated in numerous medical conditions. For example, disruption of cholinergic signal transduction has been implicated in age related central nervous system (CNS) dysfunction, such as cognitive decline and Alzheimer's disease. Alzheimer's disease is combined with, and also most likely caused by, an up to 90% degeneration of the muscarinic cholinergic neurons in nucleus basalis which project to the prefrontal cortex and hippocampus and have a general stimulatory effect on the cognitive functions, namely learning, association, consolidation and recognition, of the forebrain and hippocampus.

It is a characteristic of Alzheimer's disease that although the cholinergic neurons degenerate, the postsynaptic muscarinic receptors in the forebrain and hippocampus still exist. Muscarinic cholinergic agonists are believed to be useful in the treatment of Alzheimer's disease, in halting its progression, and in improving the cognitive functions of elderly people. In addition to treating cognitive decline, muscarinic agonists are useful as analgesic agents in the treatment of severely painful conditions, with the analgesia produced being comparable to that of opiate analgesics.

Agents that act as muscarinic receptor antagonistics are useful in the treatment of glaucoma, psychotic conditions, anxiety, mania, bipolar disorder, schizophrenia or schizophreniform conditions, depression, sleep disorders, epilepsy, cerebral ischemia, and diseases associated with altered mobility or tone of smooth muscle, such as, gastrointestinal motility disorders and chronic obstructive airways disease.

Raufman et al, 1998, Am. J. Physiol. 274 (6 Pt 1):G997–1004, disclose a possible role for the bile acid lithocholyltaurine as a partial agonist for muscarinic cholinergic receptors in gastric chief cells.

Kadlubowski et al., 1984, Acta. Physiol. Pol. September–December; 35(5–6):491–9 disclose action of select drugs on the autonomic system under the influence of the bile acids 3,12-dihydroxycholanic acid (deoxycholic), 3,7,12-trihydroxycholanic acid (cholic), and 3,7,12-triketocholanic acid (dehydrocholic).

Szkudlinski, 1984, Acta. Physiol. Pol. September–December; 35(5–6):500–8 discloses the effects of bile acids (deoxycholic, cholic, and dehydrocholic) on the action of select autonomic system drugs. Results therein suggest bile acids increase the effect of acetylcholine on the intestine.

U.S. Pat. No. 6,124,312, issued Sep. 26, 2000, to Mitch et al., discloses use of heterocyclic 2-aza-bicyclo-[2.2.1]-heptane compounds in modulating a muscarinic receptor.

U.S. Pat. No. 6,060,473, issued May 9, 2000, to Shen et al., discloses use of 7-azabicyclo-[2.2.1]-heptane and - heptene derivatives that may be administered to treat disorders associated with a decrease or increase in cholinergic activity.

U.S. Pat. No. 6,093,733, issued Jul. 25, 2000, to Villalobos et al., discloses a class of partial or full muscarinic receptor agonists useful for treatment or prevention of diseases/syndromes characterized by excessive cholinergic activity.

EP 0,301,392 (A1) published Feb. 1, 1989, Carman et al., discloses a pharmaceutical composition for intra-nasal administration comprising GO-Releasing hormone, a cholinergic agent, and a bile salt.

In spite of advancements in the art, many compounds that affect muscarinic cholinergic receptor activity are associated with side effects attributed to undesired modulation of the muscarinic cholinergic receptors. Such undesired modulation may cause effects such as, excessive salivation and gastrointestinal upset. Thus, there is a need in the art for new cholinergic agents having high potency and a favorable side effect profile.

There is another need in the art for methods of making cholinergic agents, wherein the agents are hybrid molecules derived from a progenitor cholinergic agent and a bile acid.

There is even another need in the art for compositions comprising cholinergic agents, wherein the agents are hybrid molecules derived from a progenitor cholinergic agent and a bile acid.

There is still another need in the art for methods of making such compositions.

There is yet another need in the art for methods of treating a patient having a disorder, wherein the methods comprise administration of a composition comprising a cholinergic agent, wherein the agent is a hybrid molecule derived from a progenitor cholinergic agent and a bile acid.

These and other needs will become apparent to those of skill in the art upon review of this specification, including its drawings, claims and appendix.

SUMMARY OF THE INVENTION

It is an object of the present invention to provide cholinergic agents that are hybrids synthesized from a progenitor cholinergic agent and a bile acid.

It is another object of the present invention to provide methods of making cholinergic agents, wherein the agents are hybrid molecules derived from a progenitor cholinergic agent and a bile acid.

It is even another object of the present invention to provide compositions comprising said cholinergic agents.

It is still another object of the present invention to provide methods of making such compositions.

It is yet another object of the present invention to provide methods of treating a patient having a disorder wherein the method comprises administration of a composition comprising a cholinergic agent, wherein the agent is a hybrid molecule derived from a progenitor cholinergic agent and a bile acid.

One embodiment of the present invention is directed to novel cholinergic agents. Generally the agents are hybrid/chimeric molecules synthesized from a progenitor cholinergic agent and a bile acid. The progenitor cholinergic agent may be any cholinergic agent including, but not limited to, acetylcholine, atropine, N-methylscopolamine and carbamylcholine, and a bile acid. The bile acid may be any bile acid including, but not limited to, the major bile acids, such as the cholic, deoxycholic, chenodeoxycholic, lithocholic, ursocholic and ursodeoxycholic acids. In a preferred embodiment, the progenitor cholinergic agent is acetylcholine and the bile acid is lithocholic acid. The hybrid cholinergic molecules of the invention interact with a cholinergic receptor and may function as either cholinergic agonists, or cholinergic antagonists.

Another embodiment of the present invention is directed to methods of making a hybrid/chimeric cholinergic agent. Generally the methods comprise the steps of:
 1. formylation of a bile acid→product A;
 2. product A+a progenitor cholinergic agent→product B;
 3. product B+methanesulfonic acid→hybrid cholinergic agent.

Even another embodiment of the present invention is directed to compositions comprising a cholinergic agent. Generally the compositions of the invention comprise cholinergic agents that are hybrid/chimeric molecules synthesized from a progenitor cholinergic agent and a bile acid. A particularly preferred composition of the invention comprises lithocholylcholine, a hybrid cholinergic agent synthesized from acetylcholine and lithocholic acid.

Still another embodiment of the present invention is directed to methods of making such compositions.

Yet another embodiment of the present invention is directed to methods of treating a patient. Generally, the methods comprise administering a hybrid/chimeric molecule that functions as a cholinergic agent. A particularly preferred agent of the invention is lithocholylcholine. The patient may be any mammal, but is generally a human. The method of the invention is useful for treating a patient having a medical condition wherein the sympathetic nervous system is affected.

These and other embodiments of the present invention will become apparent to those of skill in the art upon review of this specification, including its drawings, appendix, and claims.

DETAILED DESCRIPTION OF THE INVENTION

Figure 2:
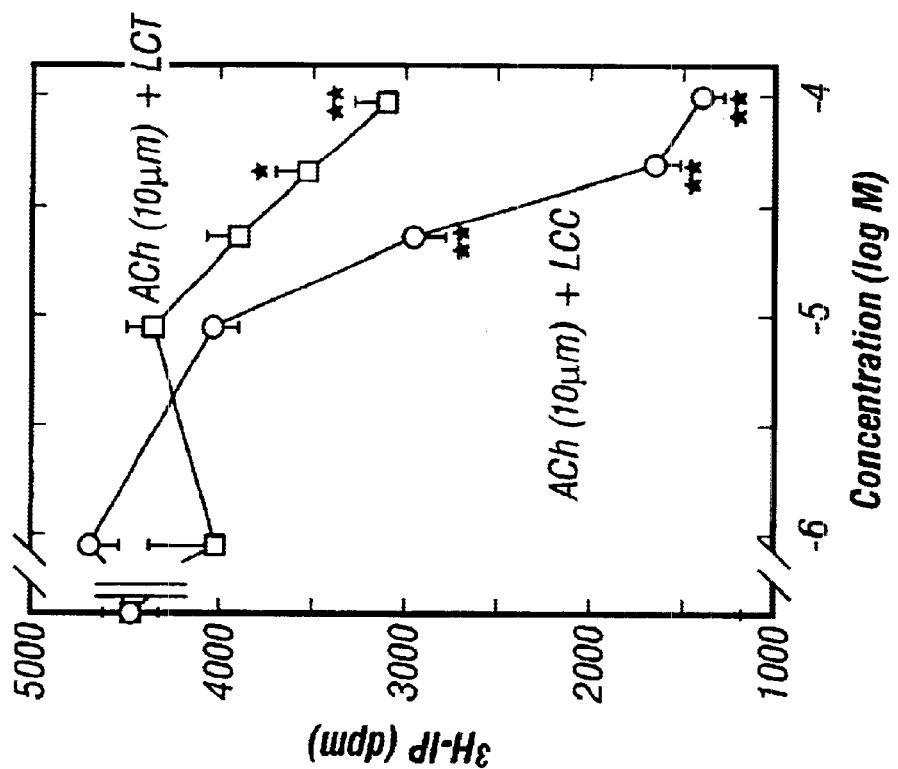
FIG. 2 provides three dimensional models of lithocholyltaurine (LCT), acetylcholine (ACh), and lithocholylcholine (LCC).

The present invention is directed to cholinergic agents, wherein the cholinergic agents are hybrid molecules. The invention is further directed to the production and utilization of the cholinergic agents of the invention, and to products and methods utilizing these agents.

As used herein, the term "hybrid" is defined as a molecule synthesized from at least two progenitor molecules, and may be used interchangeably with the term "chimeric" or "chimera". Thus, the molecules of the invention may be referred to herein as hybrid cholinergic molecules, hybrid cholinergic agents, hybrids, modified hybrid molecules, chimeric molecules, and chimeric agents. The hybrid molecules of the invention function as cholinergic agents.

As used herein, the term "cholinergic agent" refers to a molecule/agent that interacts with a cholinergic receptor. The interaction may result in an increase or a decrease in activity of the receptor (i.e., up-regulation or down-regulation, respectively). Thus, the hybrid molecules of the invention comprise hybrid cholinergic agonists and hybrid cholinergic antagonists. The interaction between the hybrid molecules of the invention and the cholinergic receptor may be a direct interaction or an indirect interaction. The cholinergic receptor may be any muscarinic or nicotinic receptor. Preferably, the receptor is a muscarinic receptor, more preferably, the M3 muscarinic receptor.

As used herein, the term "progenitor cholinergic agent" refers to the cholinergic agent/molecule used in the reaction process/method of the invention for making the hybrid molecules/hybrid cholinergic agents of the invention.

Generally the hybrid agents of the invention are hybrid molecules synthesized from a progenitor cholinergic agent and a bile acid. The hybrid molecules of the invention comprises a cholinergic moiety and a bile acid moiety. The progenitor cholinergic agent may be any cholinergic agent including, but not limited to, acetylcholine, atropine, N-methylscopolamine and carbamylcholine, and a bile acid. The bile acid may be any bile acid including, but not limited to, the major bile acids, such as the cholic, deoxycholic, chenodeoxycholic, lithocholic, ursocholic and ursodeoxycholic acids. In a preferred embodiment, the progenitor cholinergic agent is acetylcholine and the bile acid is lithocholic acid.

Generally, the hybrid cholinergic agents of the invention are more lipophilic than conventional cholinergic agents, and are therefore able to reach cellular sites that are inaccessible to conventional agents. In addition, the hybrid agents of the invention may interact with cholinergic receptors for a longer time period than do conventional agents and are therefore more effective in regulating receptor activity. Preferably the hybrid agents of the invention are at least as potent or efficacious, if not more potent or efficacious, as naturally/physiologically occurring cholinergic agents. As discussed previously, the interaction between the hybrid molecules of the invention and the cholinergic receptor may be direct or indirect.

The hybrid molecules of the invention include hybrid molecules whose structure have been altered. Altering the structure of the molecule comprises addition of chemical groups to, and/or removal of chemical groups from the hybrid molecule's structure. Techniques and reagents for modifying molecular structures are numerous and well known by those of ordinary skill in the art, and any and all such techniques and reagents are applicable herein.

The function of the modified hybrid molecule may be altered in comparison to the original, unmodified, wild-type hybrid molecule. The modified hybrid may have increased or decreased function in comparison to the wild-type molecule, and/or the modified hybrid may function as an antagonist to the wild-type molecule. In addition, the modified hybrid molecule may have an increased or decreased half-life in comparison to the wild-type hybrid. The modified hybrid molecule may be more or less chemically reactive than the wild-type hybrid making it more or less well suited for use in a composition of the invention. Further, the effective dose for the modified hybrid molecule may be more or less than that required for the wild-type molecule.

Another embodiment of the invention is directed to a method for making a hybrid cholinergic agent. Generally the method comprises the following steps:

1. formylation of a bile acid→product A;
2. product A+a progenitor cholinergic agent→product B;
3. product B+methanesulfonic acid→hybrid cholinergic agent.

As stated previously, the progenitor cholinergic agent may be any cholinergic agent including, but not limited to, acetylcholine, atropine, N-methylscopolamine and carbamylcholine, and a bile acid. The bile acid may be any bile acid including, but not limited to, the major bile acids, such as the cholic, deoxycholic, chenodeoxycholic, lithocholic, ursocholic and ursodeoxycholic acids. Each step of the synthesis process may further comprise additional agents known in the art such as buffers, catalysts, etc., that stabilize, catalyze, and/or aid the overall chemical reaction therein. The reaction steps are each carried out for a period of time and at a temperature that allows for the reaction therein to occur with maximum efficiency.

In a preferred embodiment, the bile acid utilized in step 1 is lithocholic acid, step 2 further comprises dicyclohexylithocholic acid and 4-dimethylaminopyridine, and the chimera produced in step 3 is lithocholylcholine (LCC) having a molecular mass of 462 Dalton. The hybrid molecule may be finally resuspended in any buffered solution or distilled water known in the art such as, for example, DMSO or methanol, wherein the stability of the molecule is maximized. Alternatively, the molecule may be dried and stored in pellet or powder form.

The bile acids, progenitor cholinergic agents, and additional reagents used in the reaction processes/method of the invention are well known in the art, are commercially available and their structures are known in the art. Any and all such bile acids, progenitor cholinergic agents, and reagents may be used herein.

As the hybrid molecules of the invention comprise modified hybrid molecules, the method may further comprise a step of modifying the hybrid cholinergic molecule. As discussed previously, modification of the hybrid molecule comprises altering the structure of the molecule by adding chemical groups to and/or removing chemical groups from the hybrid's structure. Techniques and reagents for modifying molecular structures are numerous and well known by those of ordinary skill in the art, and any and all such techniques and reagents are applicable herein.

Even another embodiment of the invention is directed to compositions. The compositions of the invention generally comprise a hybrid cholinergic agent. A preferred composition of the invention comprises the lithocholylcholine. The compositions of the invention further comprise a conventional pharmaceutically acceptable carrier/vehicle.

The preparation of compositions is well known to those of ordinary skill in the art. All such techniques known in the art are appropriate for use in preparing the compositions of the present invention, and are incorporated herein by reference. Additionally, the administration of the compositions of the present invention may be by any method known to one of skill in the art. Thus, administration of hybrid molecules and compositions of the present invention to a recipient may be by a route selected from oral, buccal, intra nasal, parenteral (including, subcutaneous, intradermal, intramuscular, and intravenous) and rectal. For increased efficacy, the compositions of the present invention may be administered via localized delivery to a targeted tissue. Preferably the present invention is administered orally or parenterally.

Generally the method for making a composition of the invention comprises mixing an effective quantity of a hybrid cholinergic agent of the invention together with a pharmaceutically acceptable carrier/vehicle. Pharmaceutically acceptable carriers/vehicles are well known in the art and include aqueous solutions, non-toxic occupants, including salts, preservatives, buffers and the like, propylene glycol, polyethylene glycol, vegetable oil, injectable organic esters such as ethyloleate, water, saline solutions, parenteral vehicles such as sodium chloride and Ringer's dextrose, glycerol, lipids, alcohols, and carbohydrates.

Compositions of the present invention may be of any form known in the art, such as an orally digestible form, a sterile injectable form, forms suitable for delayed release, and forms that are endemically coated. Compositions of the invention may be in solid forms, including, for example, powders, tablets, pills, granules, capsules, sachets and suppositories, or may be in liquid forms including solutions, suspensions, gels and emulsions.

Still another embodiment of the invention is directed to a method for treating a patient. Generally the method comprises administering an effective dose of a composition of the invention to a patient, wherein the composition comprises a hybrid cholinergic agent of the invention.

The methods of the invention are useful in treating a patient afflicted with at least one disorder. The disorder may be any disorder characterized by decreased or increased cholinergic function, and may be any cognitive, neurological, and/or mental disorder. Generally the disorder is any one selected from the group consisting of psychotic disorders, pain, sleep disorders, depression, Alzheimer's disease, tardive dyskinesia, Picks disease, Huntington's chorea, Frederic's ataxia, Gilles de la Pteriidae's disease, Down's Syndrome, attention-deficit disorder, multi-infarct dementia, and age-related cognitive decline (ARCED). In addition, the disorder may be in any stage of development.

The hybrid molecules/agents, compositions, and methods of the present invention are suitable for use with any patient. The patient may be any animal, such as, for example, humans, livestock, laboratory animals, household pets, and non-domestic animals such as wildlife. Preferably, the patient is a vertebrate, more preferably a mammal, and most preferably a human. Thus, the hybrid molecules/agents, compositions, and methods of the present invention have utility for a variety of users including, for example, medical doctors, veterinarians and research scientists.

The compositions and methods of the present invention may be administered to a recipient/patient as a single dose unit, or may be administered in several dose units, for a period ranging from one day to several years. The dose unit and dose schedule is dependent upon at least the severity of disorder, as well as the mode of administration. The dose unit and dose schedule may be any unit and any schedule that efficiently and effectively reduces the patient's disorder-associated symptoms. The effective dose of the compositions of the present invention may be further dependent upon the body weight (BW) of the patient. As used herein, the term "effective dose" is defined to be any dose which reduces the symptoms associated with the patient's cholinergic disorder. Thus, an effective dose is any dose which restores cholinergic signalling activity in the patient resulting in a reduction of the patient's cholinergic disorder-associated symptoms. Methods used to determine an effective dose and dose schedule are conventional and known in the art.

EXAMPLES

The invention having been generally described, the following examples are provided merely to illustrate certain embodiments of the invention. It is to be understood that the examples are not intended to limit the scope of the claims of the present invention, and should not be so interpreted.

Reagents Utilized Herein

The following is a partial list of reagents utilized herein, and the sources thereof: Dulbecco's Modified Eagle Medium, MEM non-essential amino acid, penicillin, streptomycin, and G418 were obtained from GibcoBRL; [N-methyl-$^3$H]scopolamine ([$^3$H]NMS) and $^3$H-myo-inositol were from New England Nuclear (Boston, Mass.); Carbachol was from CalBioChem; Lithocholylglycine (LCG) was from Steraloids, Inc.; all other chemicals were obtained either from Sigma or Fisher.

Example 1

Synthesis of Lithocholylcholine, a Hybrid Molecule of the Invention

Figure 1:
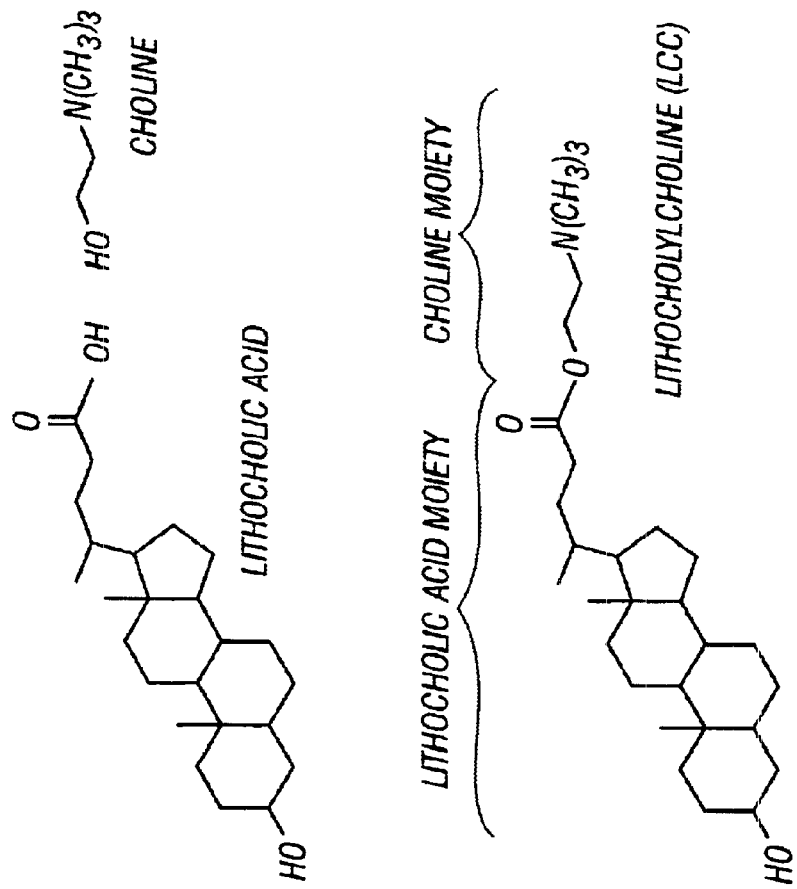
FIG. 1 provides the structure of lithocholylcholine (LCC), one hybrid cholinergic agent of the invention.

The objective of this experiment was to synthesize a hybrid cholinergic molecule of the invention. The bile acid lithocholic acid (180 mg in 6.0 ml HCOOH) was formylated to 3α-formyloxylithocholic acid and conjugated with the progenitor cholinergic agent choline-TBP (150 mg in 1.5 ml DMF), in the presence of dicyclohexylcarbodiimide (62 mg in 0.5 ml DMF) and 4-dimethylaminopyridine (4.4 mg in 0.1 ml DMF) at room temperature (RT) for an overnight incubation. The resulting molecule was deformylated by adding 2.0 ml of a solution of methanesulfonic acid/methanol (5%) and heating the mixture for 15 seconds in a microwave oven at 10% power to produce lithocholylcholine (LCC). Purity of the LCC compound was verified by thin layer chromatography (TLC). The structure of LCC was confirmed by mass spectrometry (MS). The LCC may be dried and stored in pellet/powder form, or dried and resuspended in methanol or DMSO. FIG. 1 shows the structure of lithocholic acid, choline, and lithocholycholine.

Example 2

Interaction of LCC with CHO Cells Expressing M3 Muscarinic Receptors

The objective of this experiment was to evaluate whether LCC interacted with muscarinic M3 receptors. CHO cells expressing M3 muscarinic receptors were obtained from the American Type Culture Collection (ATCC), MD. The interaction of LCC with the M3 receptors was determined by an assay which measures inhibition of $^3$H-N-methylscopolamine ($^3$H-NMS) binding to the M3 receptor. Acetylcholine, carbachol, lithocholyltaurine and lithocholylglycine were included in the assay as positive controls. Lithocholyltaurine and lithocholylglycine are physiological conjugates of lithocholic acid.

Binding of $^3$H-NMS to CHO cells was performed as described in Sutliff et al., (1989, Am. J. Physiol. 257 (Gastrointest. Liver Physiol. 20) G226–G234) with the following modifications. $5\times10^5$ CHO cells (0.5 ml) were incubated for 45 minutes at 37° C. with 0.6 nM $^3$H-NMS alone or with unlabeled ligand. Nonspecific binding was determined in the presence of 10.0 μM unlabeled NMS. The reaction was terminated by centrifuging 0.5 ml of cell suspension at 10,000 g for 7 minutes at room temperature. 100 μl of supernatant was sampled for determination of free ligand concentration, and the remaining liquid was carefully decanted. The cell pellet was washed, drained, and dissolved in 100 μl Soluene 350. Ecosint A was added, and the radioactivity in the tubes was measure in a liquid scintillation counter (1214 Rackbeta, LKB/Wallac, Gaithersburg, Md.).

The results from at least three such binding assays are as follows (mean±SE):

| AGENT | IC50 (μM) |
| --- | --- |
| LCC | 6.4 ± 0.8 |
| Acetylcholine | 15.2 ± 4.1 |
| Carbachol | 399.2 ± 43.3 |
| Lithocholyltaurine | 165.1 ± 38.5 |
| Lithocholylglycine | 228.3 ± 41.2 |

The results of this experiment reveal that LCC is about 2 times more potent than acetylcholine and about 60 times more potent than carbachol at inhibiting $^3$H-NMS binding to M3 muscarinic receptors. Thus, LCC is an M3 muscarinic receptor antagonist.

Example 3

Measurement of LCC Effects on Downstream M3 Receptor Activity

Post-receptor (downstream) actions of LCC were determined by measuring increases in inositol phosphates (IP) after incubating cells with 3H-myo-inositol. CHO cell inositol 1,4,5-triphosphate (IP3) was determined by the methods of Hu and El-Fakahany (1990, Mol. Pharmacol. 38:895–903) and Labarca et al., (1987, Methods Enzymol. 141:192–201). $5\times10^4$ cells/well were incubated with 1.0 μCi/ml myo-[2-$^3$H]inositol for 24 hour at 37° C., treated with 20 mM LiCl for 30 minutes at 37° C. Cells were then incubated with the test agents for 30 minutes at 37° C. The IP3 fraction was separated by ion-exchange chromatography (AG2 X8 resin), and the dpm in this fraction were determined by liquid scintillation.

FIG. 2 shows the effects of different concentrations of either lithocholylcholine (LCC), or lithocholyltaurine (LCT) on 10.0 μM acetylcholine (ACh)-induced IP formation in CHO cells expressing the M3 muscarinic receptor (CHO-M3 cells). Although LCC alone was found to not alter IP formation in CHO-M3 cells, LCC inhibits ACh-induced IP formation. As clearly shown in FIG. 3, LCC inhibits ACh-induced IP formation in CHO-M3 cells to an overall greater extent than do equal concentrations of LCT, a partial muscarinic M3 receptor agonist. The highest LCC concentration tested (0.1 mM) reduced ACh-induced IP production by 80%, thereby confirming competition of LCC and ACh for the same receptor, indicating interaction of LCC and ACh with the same receptor. Thus, LCC is an M3 muscarinic receptor antagonist.

Figure 3:
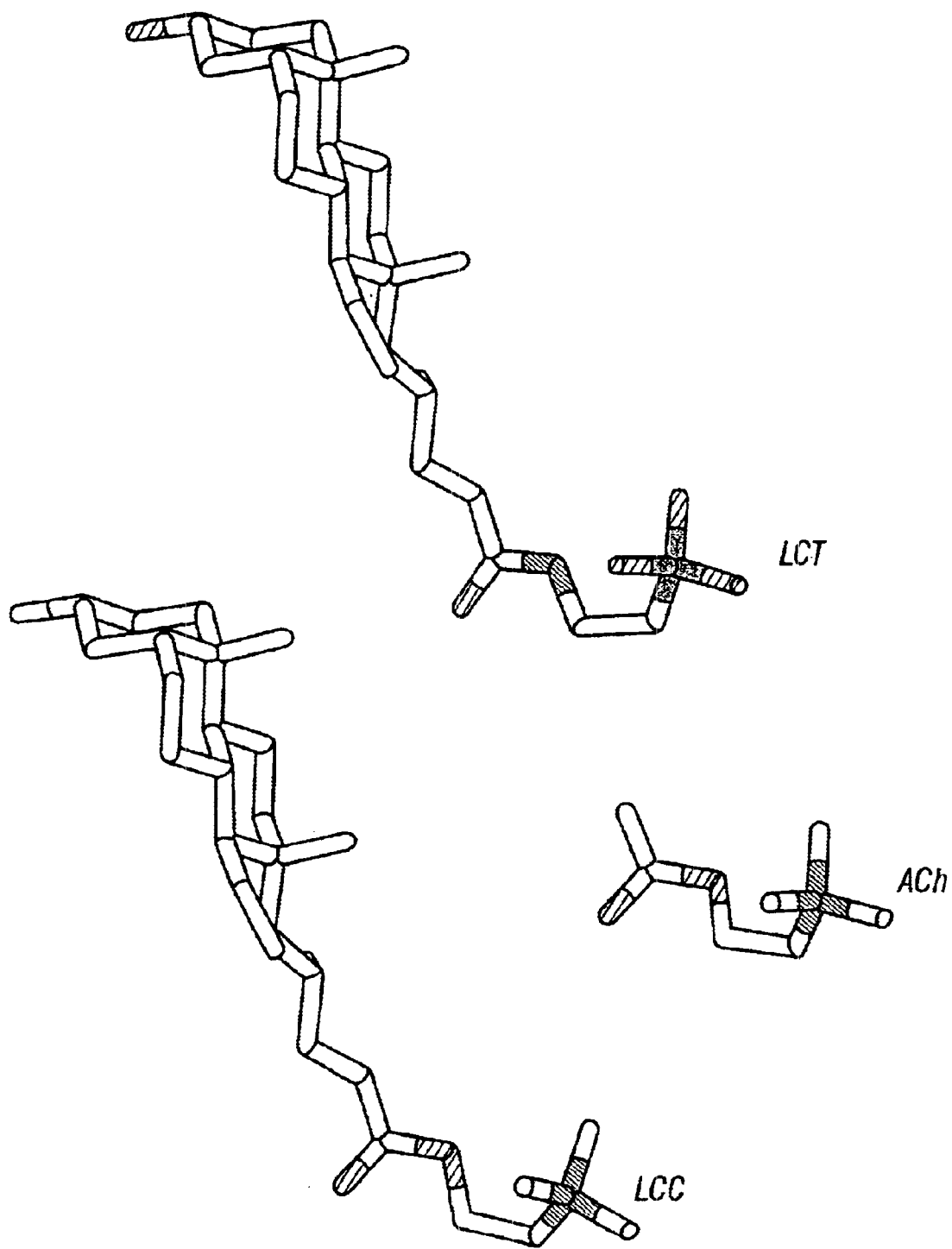
FIG. 3 illustrates the effect of LCC on acetylcholine-induced inositol phosphate (IP) formation in CHO-M3 cells.

FIG. 3 shows three-dimensional models of lithocholyltaurine (LCT), acetylcholine (ACh), and lithocholylcholine (LCC).

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein, but rather that the claims be construed as encompassing all the features of patentable novelty which reside in the present invention, including all features which would be treated as equivalents thereof by those skilled in the art to which this invention pertains.

All references cited in the present application, including journal articles, U.S. and foreign patents and patent applications, are incorporated herein by reference.

We claim:

1. A method for making a hybrid molecule the method comprising the steps of:
   a) formylating a bile acid;
   b) conjugating the product of step a) with a cholinergic agent; and
   deformylating the product of step b) by addition of methane sulfonic acid to produce a hybrid molecule
   wherein said hybrid molecule comprises a bile acid moiety and a cholinergic moiety and wherein said hybrid molecule is of the formula

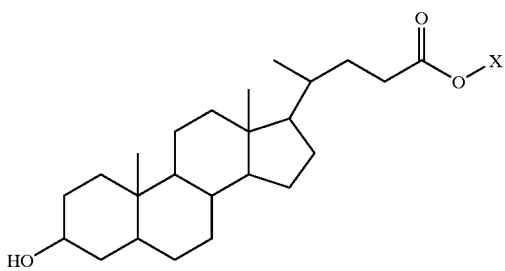

wherein X is said cholinergic moiety and is selected from the group consisting of acetylcholine, atropine, N-methylscopolamine and carbamylcholine.

2. The method of claim 1 wherein the bile acid is lithocholic acid, and wherein the product of step a) is 3α-formyloxylithocholic acid.

3. The method of claim 1 wherein the cholinergic agent is acetylcholine.

4. The method of claim 1 wherein step b further comprises dicyclohexylithocholic acid and 4-dimethylaminopyridine.

5. The method of claim 1 wherein the hybrid molecule is lithocholylcholine.

6. A method for treating a patient affected with at least one cholinergic disorder, the method comprising the step of:
   a) administering to said patient an effective dose of a composition, wherein the composition comprises an effective quantity of a hybrid cholinergic agent,
   wherein said agent is a hybrid molecule comprising a bile acid moiety and a cholinergic moiety wherein said agent is of the formula

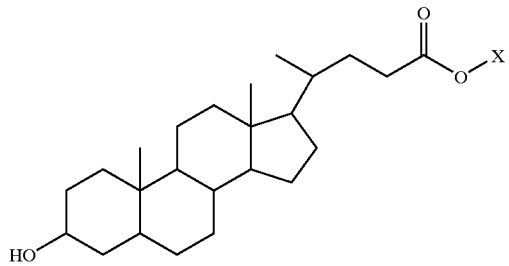

wherein X is said cholinergic moiety and is selected from the group consisting of acetylcholine, atropine, N-methylscopolamine and carbamylcholine.

7. The method of claim 6 wherein said cholinergic disorder is in any stage of development.

8. The method of claim 6 wherein the patient is afflicted with at least one disorder selected from the group consisting of psychotic disorders, pain, sleep disorders, depression, Alzheimer's disease, tardive dyskinesia, Picks disease, Huntington's chorea, Frederic's ataxia, Gilles de la Pteriidae's disease, Down's Syndrome, attention-deficit disorder, multi-infarct dementia, and age-related cognitive decline (ARCED), and wherein the disorder is in any stage of development.

9. The method of claim 6 wherein the patient is a human.

10. The method of claim 6 wherein the bile acid is selected from the group consisting of cholic, deoxycholic, chenodeoxycholic, lithocholic, ursocholic and ursodeoxycholic acids.

11. The method of claim 10 wherein the hybrid cholinergic agent is lithocholylcholine.

* * * * *